(12) United States Patent
Newbold et al.

(10) Patent No.: US 9,389,151 B2
(45) Date of Patent: Jul. 12, 2016

(54) FIXED VOLUME ASEPTIC SAMPLING VALVE FOR SAMPLING FROM ENCLOSED CONTAINERS

(71) Applicant: Bend Research, Inc., Bend, OR (US)

(72) Inventors: David Dixon Newbold, Bend, OR (US); Douglas Lee Millard, Bend, OR (US); Erwin Yaokui Yu, Ballwin, MO (US); Paul T. Jeffers, Frankfield (IE); Jeffrey W. Weber, Portage, MI (US)

(73) Assignee: Bend Research, Inc., Bend, OR (US)

( * ) Notice: Subject to any disclaimer, the term of this patent is extended or adjusted under 35 U.S.C. 154(b) by 326 days.

(21) Appl. No.: 14/072,228

(22) Filed: Nov. 5, 2013

(65) Prior Publication Data

US 2014/0123775 A1    May 8, 2014

Related U.S. Application Data

(60) Provisional application No. 61/722,743, filed on Nov. 5, 2012.

(51) Int. Cl.
*G01N 1/10* (2006.01)
*C12M 1/26* (2006.01)

(52) U.S. Cl.
CPC ............... *G01N 1/10* (2013.01); *C12M 33/04* (2013.01); *G01N 2001/1037* (2013.01)

(58) Field of Classification Search
CPC   G01N 1/10; G01N 35/1097; G01N 2001/205
See application file for complete search history.

(56) References Cited

U.S. PATENT DOCUMENTS

| 3,379,216 A | 4/1968 | Mercier |
| 3,713,988 A | 1/1973 | Dawson et al. |
| 3,771,562 A | 11/1973 | Curran |
| 3,807,906 A | 4/1974 | Breit |
| 4,347,877 A | 9/1982 | Hoiss |
| 4,548,088 A | 10/1985 | Hood, Jr. |
| 4,889,812 A | 12/1989 | Guinn et al. |
| 4,918,019 A | 4/1990 | Guinn |
| 5,075,905 A * | 12/1991 | Rutherford ............. E03C 1/282 137/247.51 |
| 5,296,197 A * | 3/1994 | Newberg ............... F16K 41/103 137/240 |
| 5,630,935 A | 5/1997 | Treu |
| 5,948,998 A * | 9/1999 | Witte ..................... C12M 33/00 73/863.57 |
| 6,085,602 A | 7/2000 | Schorn et al. |
| 6,133,022 A | 10/2000 | Newberg |
| 6,423,548 B1 | 7/2002 | Newburg et al. |
| 6,491,283 B2 | 12/2002 | Newberg |

(Continued)

FOREIGN PATENT DOCUMENTS

| FR | 2617286 | 12/1988 |
| WO | WO 2006/086489 | 8/2006 |
| WO | WO 2011/038008 | 3/2011 |

OTHER PUBLICATIONS

Benz. "Bioreactor Designs for Chemical Engeneers" Chem. Eng. Progress 107.8 (2011): 21-26.

(Continued)

*Primary Examiner* — David A Rogers
(74) *Attorney, Agent, or Firm* — Klarquist Sparkman, LLP

(57) ABSTRACT

A sample can be collected from an enclosed container by opening a sample collection valve and drawing the sample from the enclosed container. After delivery of the sample out of a fluid flow path, a sanitizing fluid can be directed along the fluid flow path to sanitize the fluid flow path.

20 Claims, 17 Drawing Sheets

(56) References Cited

U.S. PATENT DOCUMENTS

| | | | |
|---|---|---|---|
| 6,516,677 B1 * | 2/2003 | Suter | G01N 1/10 73/863.85 |
| 6,637,277 B2 * | 10/2003 | Gamache | G01N 1/16 73/863.33 |
| 6,821,773 B1 | 11/2004 | Newberg | |
| 7,192,003 B2 | 3/2007 | Hoobyar et al. | |
| 7,389,792 B2 | 6/2008 | Newberg | |
| 7,601,545 B2 * | 10/2009 | Barringer, Jr. | B01D 61/14 210/798 |
| 7,955,843 B2 * | 6/2011 | Barringer, Jr. | B01D 61/142 137/240 |
| 8,549,934 B2 * | 10/2013 | Biksacky | G01N 1/2035 73/863.01 |
| 2002/0036017 A1 | 3/2002 | Leys et al. | |
| 2004/0259241 A1 * | 12/2004 | Barringer, Jr. | B01D 61/142 435/309.2 |
| 2007/0039653 A1 | 2/2007 | Maggard | |
| 2007/0128087 A1 | 6/2007 | Cannizzaro et al. | |
| 2007/0131289 A1 | 6/2007 | Pataki | |
| 2008/0032380 A1 | 2/2008 | Kleis et al. | |
| 2008/0314450 A1 * | 12/2008 | Hawker | A61L 2/18 137/2 |
| 2009/0038419 A1 | 2/2009 | Hiller et al. | |
| 2009/0178495 A1 | 7/2009 | Steigmiller et al. | |
| 2009/0199904 A1 | 8/2009 | Babbitt et al. | |
| 2010/0043883 A1 | 2/2010 | Yu et al. | |
| 2010/0047122 A1 | 2/2010 | Barringer, Jr. | |
| 2010/0102008 A1 | 4/2010 | Hedberg | |
| 2010/0236340 A1 | 9/2010 | Lee et al. | |

OTHER PUBLICATIONS

Daken Stainless Products: "Keofitt W15 Sample Valves", (Jan. 1, 2005), Available at http://www.keofitt-uk.com/865541.htm [last accessed on Jul. 6, 2012].

Daken Stainless Products: "Keofitt W15 Sample Valves", (Jan. 1, 2005), Available at http://www.keofitt-uk.com/865541.htm [last accessed Oct. 19, 2015].

* cited by examiner

Assembly

Assembly

Liquid Side

Air Side

Air Side

Air Side

US 9,389,151 B2

FIXED VOLUME ASEPTIC SAMPLING VALVE FOR SAMPLING FROM ENCLOSED CONTAINERS

CROSS-REFERENCE TO RELATED APPLICATION

This application claims the benefit of U.S. Provisional Application No. 61/722,743, which was filed on Nov. 5, 2012 and is incorporated herein by reference in its entirety.

FIELD

The present disclosure is directed to an aseptic sampling valve and methods of using the same.

BACKGROUND

Obtaining samples from containers or other systems that support biologically and/or chemically active environments can require complex and careful sampling procedures to avoid contamination of the containers or the environment itself. For example, most bioreactors require frequent sampling (e.g., one or more times a day) to monitor and control the conditions and levels of nutrients needed for cell growth. To reduce the risk of contamination within such systems, conventional sampling techniques generally require operators to perform multiple, labor-intensive steps.

SUMMARY

In some embodiments, the sampling systems and methods disclosed herein provide consistent sampling procedures for obtaining samples of a desired quality, while reducing the risk of contamination of the bioreactor and the need for labor-intensive operator attention.

A sampling system for collecting a fluid sample from an enclosed container is provided. The system can include (a) a sanitizing fluid inlet valve operable between an open position and a closed position; (b) a gas inlet valve operable between an open position and a closed position; (c) a sample collection valve operable between an open position and a closed position; (d) an outlet valve operable between an open position and a closed position; (e) a fixed volume reservoir; (f) a second outlet valve operable between an open and closed position; and (g) a fluid flow path interconnecting (a)-(f). When (a), (b), and (d) are in the closed position, and (f) is in the open position, (c) can be in the open position to withdraw a sample from the enclosed container into the reservoir along a first portion of the fluid flow path. When (a), (c), and (f) are in the closed position, and (b) is in the open position, the sample can be discharged from the reservoir along a second portion of the fluid flow path through (d). When (a) is in the open position and (b) and (c) are in the closed position, a sanitizing fluid can be introduced into the fluid flow path through (a) to sanitize at least the first portion of the fluid flow path.

In some embodiments, when (a) is in the open position, and (b) and (c) are in the closed position, the sanitizing fluid also sanitizes the reservoir. In other embodiments, (a) is at an upstream portion of the fluid flow path and (d) is at a downstream portion of the fluid flow path, and the sanitizing fluid can flow through the fluid flow path from (a) to (d) to sanitize the fluid flow path between (a) and (d). In other embodiments, (a)-(f) are interconnected along the fluid flow path from the upstream portion to the downstream portion in the following order: (a), (b), (c), (e), (d), and (f). The reservoir can include a pump that is configured to draw the sample into the reservoir through a reservoir inlet and direct the sample out of the reservoir through a reservoir outlet. In other embodiments, the drawing of the sample into the fixed volume reservoir is achieved as a result of pressure differentials and the bioreactor is maintained under pressure.

In other embodiments, a second outlet valve (f) can be located downstream of the first outlet valve (d). When (a) is in the open position and (b), (c), and (d) are in the closed position, the sanitizing fluid can flow along the fluid flow path between (a) and the second outlet valve to sanitize portions of the fluid flow path in the vicinity of (c) and (d). The second outlet valve (f) can be a variable back-pressure regulator. In some embodiments, the second outlet valve is a thermostatically-controlled valve.

In other embodiments, when (a), (c), and (d) are in the closed position, and (b), and (f) are in the open position, gas can be introduced into the fluid flow path through (b) to purge the sanitizing fluid from at least the first and second portions of the fluid flow path. In some embodiments, the gas can function to cool the valve in a case where the sanitizing fluid is hot (e.g., steam). The sample collection valve can include a valve stem with a tapered sealing member. A portion of the valve stem can extend into the fluid flow path when the sample collection valve is in the closed position, such that sanitizing fluid introduced into the fluid flow path by the sanitizing fluid inlet valve will flow past the portion of the valve stem that extends into the fluid flow path.

In another embodiment, a method of collecting a fluid sample from an enclosed container is provided. The method can include opening a sanitizing fluid inlet valve and directing sanitizing fluid downstream through a fluid flow path past a closed sample collection valve and an open first outlet valve, and discharging the sanitizing fluid out a second outlet valve, with the second outlet valve being located downstream of the first outlet valve. A sample collection valve can be opened while the sanitizing fluid inlet valve and first outlet valve (and the gas inlet valve) are closed and a fluid sample can be drawn from the enclosed container into a fixed volume reservoir along a first portion of the fluid flow path. The fluid sample can be directed out of the reservoir along a second portion of the fluid flow path and discharged out of the first outlet valve while the sanitizing fluid inlet valve and sample collection valve are closed. For a long distance embodiment, air can be pumped following the sample, allowing a relatively small volume sample to be pumped long distances.

In some embodiments, after discharging the sanitizing fluid but before drawing the fluid sample, a gas inlet valve is opened and a gas is directed downstream through the fluid flow path past the closed sample collection valve and through the first open outlet valve. The gas can be discharged through the second outlet valve to purge the sanitizing fluid from at least the first and second portions of the fluid flow path. The reservoir can include a pump that is configured to draw the sample into the reservoir through a reservoir inlet and direct the sample out of the reservoir through a reservoir outlet.

In another embodiment, a method of collecting a sample from an enclosed container is provided. The method can include directing a sanitizing fluid through a fluid flow path to sanitize or sterilize the fluid flow path. The fluid flow path can have a gas inlet port downstream of the sanitizing fluid inlet, a sample inlet port downstream of the gas inlet port, and a sample dispensing port downstream of the sample inlet port. The sanitizing fluid can be directed through the fluid flow path while the sample dispensing port is closed, and the sanitizing fluid can be exhausted through a control valve. Gas can be directed through the gas inlet port and into the fluid flow path while the sample dispensing port is closed. The gas can be exhausted through the control valve. A sample can be drawn into the fluid flow path from the enclosed container through the sample inlet port, and the sample can be dispensed out of the fluid flow path through the sample dispensing port. Additional sanitizing fluid can be directed through the fluid flow path to re-sanitize or re-sterilize the fluid flow path while the sample dispensing port is closed.

In some embodiments, drawing and dispensing the sample comprises activating a fixed volume reservoir to draw at least a portion of the sample into a chamber of the fixed volume reservoir and dispense the portion of the sample from the chamber of the fixed volume reservoir to the sample dispensing port. In other embodiments, a back pressure can be provided by the control valve while the sanitizing fluid is directed through the fluid flow path to sanitize or sterilize the fluid flow path. The control valve can include a diaphragm valve and the back pressure can be provided by increasing air pressure on the diaphragm valve. In some embodiments, the control valve can direct sample to an end receiver/analyzer. The closure of the sample inlet port can include moving a sealing tip of a valve stem so that the sealing tip engages with the sample inlet port. When the sealing tip is engaged with the sample inlet port, at least a portion of the valve stem can extend into the fluid flow path.

In some embodiments, the sampling system is made using materials that have low heat transfer coefficients. In some embodiments, the sampling system is made using polymeric materials, such as thermoplastics and thermosetting materials. In some embodiments, the sampling system is made using composite materials. In some embodiments, the sampling system is formed by injection molding. In some embodiments, the sampling system is formed by machining and drilling.

In some embodiments, the sampling system is modular in design, allowing selection of appropriate fittings for connecting to a wide variety of apparatuses. In some embodiments, the fixed volume reservoir is modular, allowing selection of a reservoir suitable for the amount of sample to be withdrawn from the enclosed container. In some embodiments the sampling system is compact to (1) reduce the hold-up volume of the sampling system, (2) allow rapid sanitizing of the sampling system, (3) allow for rapid removal of a sample from the enclosed container, or (4) any combination of (1), (2), or (3).

In some embodiments, a sample tube can dip down into the reactor from overhead allowing for the sampling into reactors above the liquid level in the container. This arrangement can be particularly helpful in a process development scale reactor.

In some embodiments, the fixed volume reservoir is designed to minimize the volume of gas that remains in the sampling system after discharge from the sampling system. In some embodiments, the ratio of the sample volume collected to the hold-up volume of the sampling system is greater than 10:1, greater than 20:1, or even greater than 50:1.

In some embodiments, the fixed volume reservoir is designed to push the sample collected out of the reservoir using a working fluid. In some embodiments, a positive pressure can be used via a working fluid. In other embodiments, the system can create the positive pressure without a working fluid, such as by using a syringe pump. In some embodiments, the pressure in the feed tank can be used to fill the reservoir, which is hooked to a piston—which can be pressurized (air or hydraulic fluid) to discharge the sample from the reservoir.

In some embodiments, the fixed volume reservoir is designed to pull the sample from the enclosed container into the reservoir by applying a negative pressure on the fixed volume reservoir. This can be particularly useful in systems with a draw tube from the top of the reactor—especially for small volume or development/experimental reactors, which may not have a port located on the bottom of the bioreactor.

In some embodiments, pumps (e.g., a diaphragm pump, peristaltic pump, gear pump) can be provided in fluid contact with the fluid flow path to push or pull a sample into the reservoir and/or to discharge the sample from the reservoir. The pump can be positioned along the fluid flow path so that it can cause a positive or negative pressure sufficient to push or pull the sample as desired. Pumps can be positioned downstream of the sample collection valve, such as between the sample collection valve and the reservoir, or downstream of reservoir along the waste path. Alternatively, pumps can be provided upstream of the sample collection valve, such as between the sample collection valve and a valve associated with a sanitizing fluid.

The foregoing and other objects, features, and advantages of the invention will become more apparent from the following detailed description, which proceeds with reference to the accompanying figures.

DETAILED DESCRIPTION

Various embodiments of sampling systems and their methods of use are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

The terms "upstream" and "downstream" are not absolute terms; instead, those terms refer to the direction of flow of fluids within a channel or pathway. Thus, with regard to a structure through which a fluid flows, a first area is "upstream" of a second area if the fluid flows from the first area to the second area. Likewise, the second area can be considered "downstream" of the first area.

Unless otherwise indicated, all numbers expressing quantities of ingredients, properties such as molecular weight, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Figure 1:
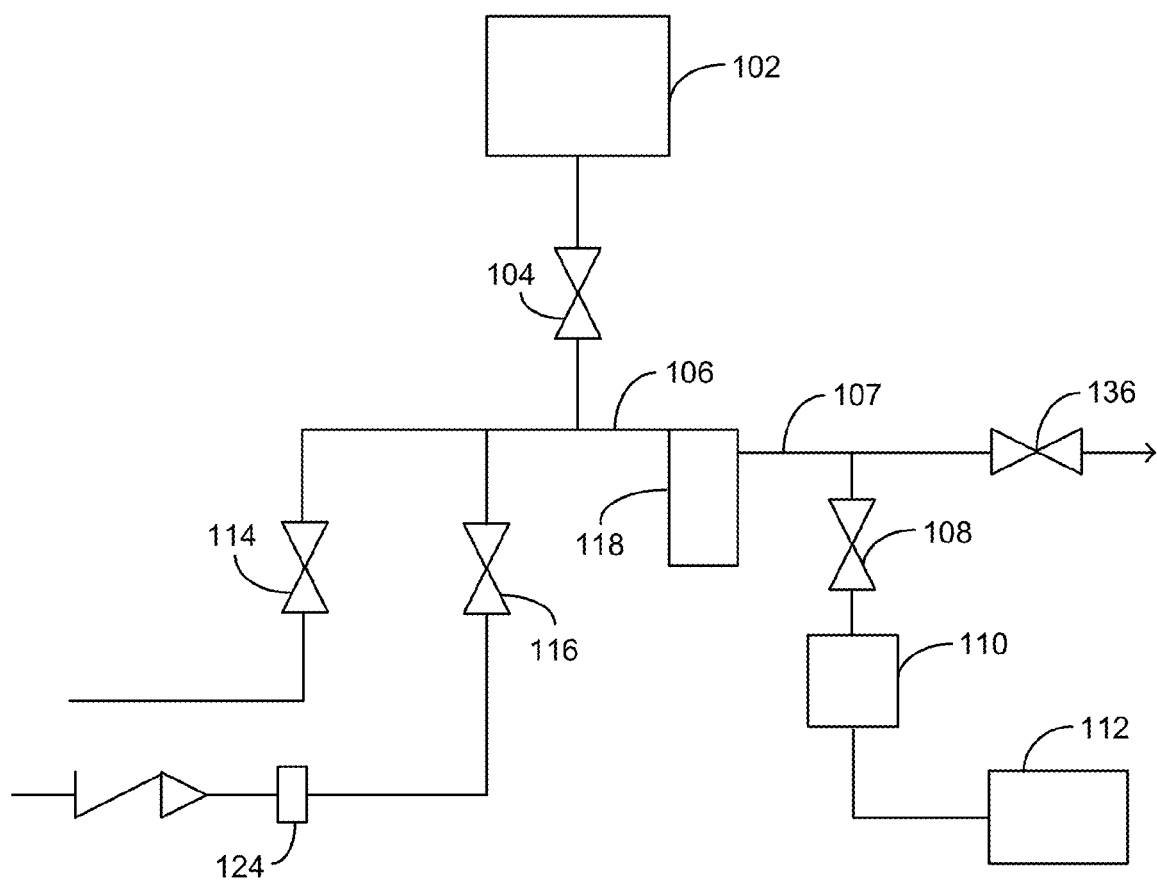
FIG. 1 illustrates a schematic view of a sampling system for obtaining samples from enclosed containers.

FIG. 1 illustrates a sampling system 100 for obtaining a sample from a bioreactor 102 or other similar containers or systems that support biologically and/or chemically active environments. Sampling system 100 includes a sample collection valve 104 that can open to allow a sample to enter a fluid flow path 106. The sample can be delivered along the flow path 106 to an outlet valve 108. Outlet valve 108 can open or close to allow or restrict, respectively, the flow of samples through outlet valve 108. After the sample exits outlet valve 108, the sample can be directed into an isolated chamber or container 110 for analysis, processing, and/or delivery to another system for analysis and/or processing. For example, the sample can be directed from chamber 110 to an automated analyzer 112, such as a bioprofile analyzer available from Nova Biomedical of Waltham, Mass.

The samples that are dispensed from outlet 108 for analysis or processing are desirably representative of the materials in bioreactor 102 at the time the sample was taken. To reduce the risk of contamination, dilution, or alteration of the composition of the samples taken from sample collection valve 104 and delivered through flow path 106, a sanitizing fluid can be delivered through a portion of flow path 106 that comes into contact with the samples.

To introduce the sanitizing fluid into flow path 106, a sanitizing fluid inlet valve 114 is provided upstream of sample collection valve 104. Sanitizing fluid inlet valve 114 is operable between a closed position that restricts fluid flow through sanitizing fluid inlet valve 114 and an open position that allows fluid flow through sanitizing fluid inlet valve 114. In one embodiment, the sanitizing fluid comprises steam. In some embodiments, some or all of the valves can be biased closed.

In one embodiment, the sanitizing fluid is any fluid that can sanitize, disinfect, or sterilize the valve. The sanitizing fluid can be a liquid, a gas, or a combination thereof. Sanitizing fluids include steam, ethylene oxide, glutaraldehyde, formaldehyde, formalin, chlorine gas, hypochlorite, bromine, hypobromite, iodine, hypoiodite, bromine chloride, chlorine dioxide, ozone, hydrogen peroxide, monochloramine, dichloramine, trichloramine, quatinary ammonium salts, ethanol, 70% ethanol/water, isopropanol, 70% isopropanol/water, peroxyacetic acid, and peracetic acid. In one embodiment, the sanitizing fluid is steam. In another embodiment, the sanitizing fluid is ethylene oxide. In another embodiment, the sanitizing fluid is glutaraldehyde.

A gas inlet valve 116 can also be provided upstream of sample collection valve 104 to deliver a gas through flow path 106. The gas can eliminate and/or reduce the amount of sanitizing fluid remaining within flow path 106 after flow path 106 is exposed to the sanitizing fluid. The sanitizing fluid can clean the path and/or remove any material from previous samples in the area contacted by the sanitizing fluid. Gas inlet valve 116 is operable between a closed position that restricts the flow of gas through gas inlet valve 116 and an open position that allows the flow of gas through gas inlet valve 116. In one embodiment, the gas comprises compressed air.

To draw a sample from bioreactor 102, a reservoir, such as a fixed volume reservoir 118, can be provided downstream of sample collection valve 104 for receiving the sample.

The sample can be drawn into the fixed volume reservoir 118 along flow path 106 and discharged from flow path 107.

As shown by dotted lines in FIG. 1, at least a portion of sampling system 100 can comprise a unitary structure 125. Thus, for example, unitary structure 125 can comprise sample collection valve 104, sanitizing fluid inlet valve 114, gas inlet valve 116, and at least a portion of the fluid flow path. In one embodiment, the entire flow path between the sanitizing fluid inlet valve 114 and the outlet valve 108 is internal to the unitary structure 125.

Figure 2A:
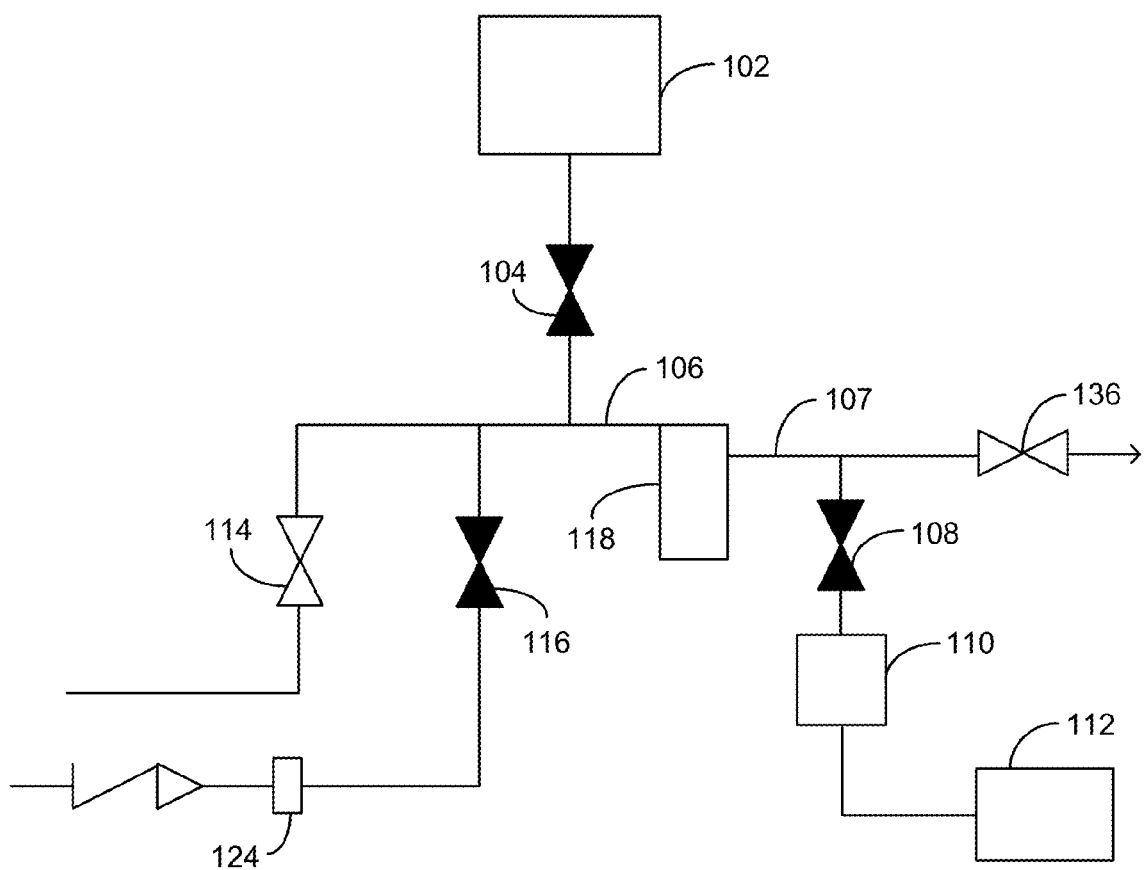
FIGS. 2A-2C illustrate schematic views of a system for obtaining samples from enclosed containers.
Figure 2B:
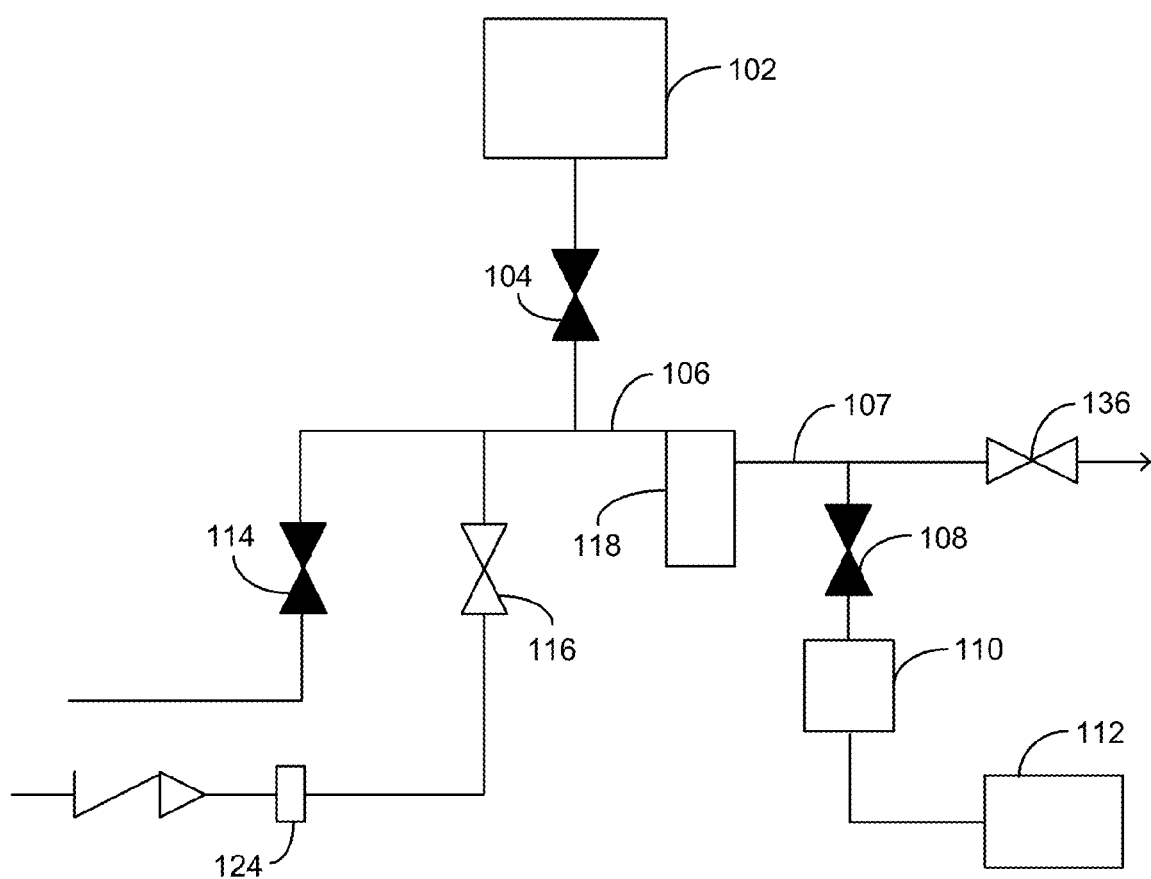
Figure 2C:
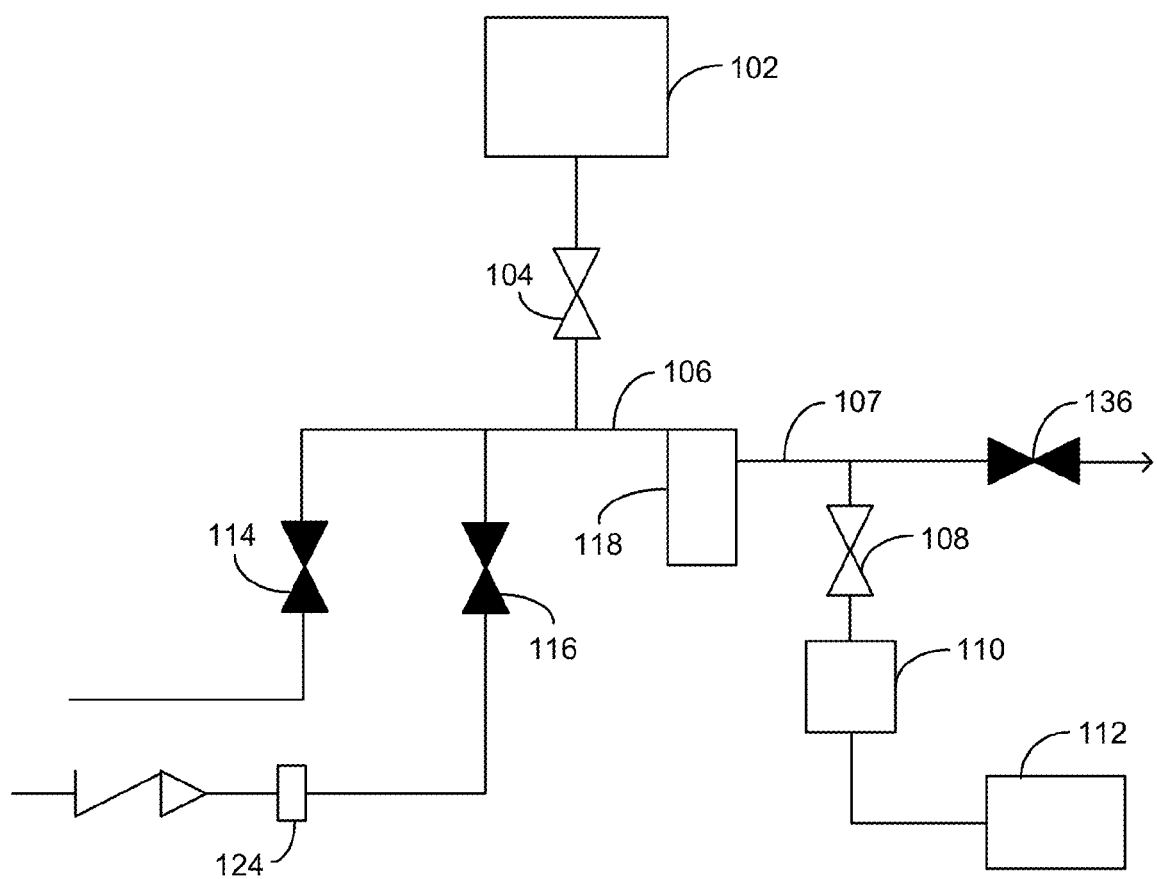

FIGS. 2A-2C are schematic representations of the operation of sampling system 100. As described in more detail below, sampling system 100 can be inserted into bioreactor 102 and can operate to sanitize or sterilize a flow path from the point of insertion with bioreactor 102 through the closed pathway of flow path 106 and 107. By being able to sanitize or sterilize the entire path downstream of the insertion point of sampling system 100 into bioreactor 102, the possibility of contaminating bioreactor 102 and/or the samples captured from bioreactor 102 is reduced.

FIG. 2A illustrates a sanitizing procedure in which a sanitizing fluid (e.g., steam) is directed into flow path 106 through an open sanitizing fluid inlet valve 114. As shown in FIG. 2A, sanitizing fluid is directed along flow path 106, including along the portions of flow path 106 that are in contact with samples that are drawn from bioreactor 102 and dispensed from flow path 106. For example, sanitizing fluid is directed along flow path 106 past sample collection valve 104, through fixed volume reservoir 118, through flow path 107, and out outlet valve 108. As sanitizing fluid comes into contact with the internal surfaces that define flow path 106 and flow path 107, those surfaces are sanitized or sterilized.

Referring now to FIG. 2B, sanitizing fluid inlet valve 114 is closed and gas inlet valve 116 is opened to allow a gas 122 (e.g., air) to enter flow path 106. As shown in FIG. 2B, gas 122 can also be directed along flow path 106, through fixed volume reservoir 118, including along the flow path 107 that sanitizing fluid contacts. In this manner, any remaining sanitizing fluid can be purged from flow path 106, fixed volume reservoir 118, and flow path 107. If desired, a filter 124 (e.g., a sterile air filter) can be provided upstream of gas inlet valve 116 to ensure that the gas 122 that enters flow path 106 is substantially free of impurities and/or contaminants.

FIG. 2C illustrates the operation of fixed volume reservoir 118 to draw a sample from bioreactor 102 through open sample collection valve 104. Sample is then discharged through outlet valve 108 to be captured for analysis and/or further processing.

Referring again to FIG. 1, as sample is discharged through outlet valve 108, it can be delivered to chamber 110. To facilitate delivery of sample to chamber 110, another valve 136 can be provided downstream of outlet valve 108. Valve 136 can be configured to open to allow the discharge of waste. The discharged waste can include, for example, sanitizing fluid and purging gas that has traveled along the flow path 106 and flow path 107 to sanitize and purge excess sample materials from flow path 106 and flow path 107. If desired, an additional back pressure valve or check valve can be provided downstream of valve 136.

Alternatively, valve 136 can comprise a control valve that can be configured to provide a back pressure to cause sample to be directed into chamber 110 and to provide a desired back pressure along flow path 106 and flow path 107 to facilitate the sanitizing process (e.g., FIG. 2A) and the purging process (e.g., FIG. 2B). As described elsewhere herein, if valve 136 is a control valve, it can be operable between on/off positions that permit fluid flow through the valve and that restrict fluid flow through the valve, respectively.

Figure 3A:
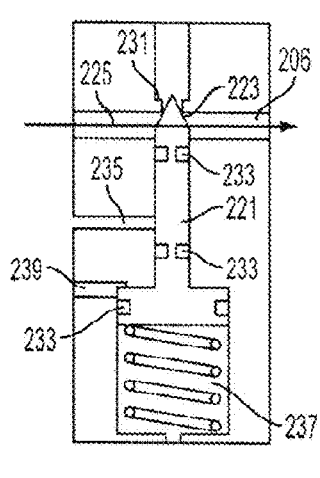
FIGS. 3A-3C illustrate enlarged views of exemplary valves that can be used with a sampling system.
Figure 3B:
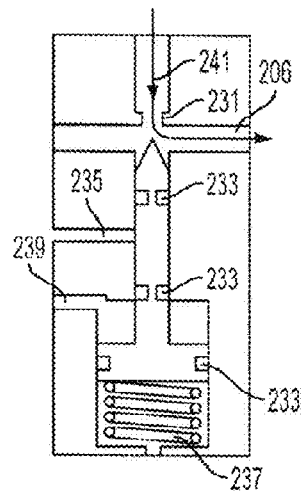
Figure 3C:
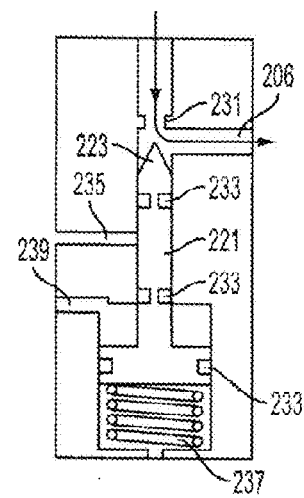

FIGS. 3A-3C illustrate enlarged views of exemplary valves that can be used with the systems disclosed in FIGS. 1 and 2A-2C. For example, FIGS. 3A and 3B illustrate a three-way bypass flow valve that can move between a closed configuration (FIG. 3A) and an open configuration (FIG. 3B). In FIG. 3A, valve stem 221 is shown extending into flow path 206 with sealing member 223 closing a port 231 (e.g., a gas inlet port, a sample collection inlet port, a sample collection outlet port) into flow path 206. In the closed configuration, fluid can flow past valve stem 221 as shown by arrow 225. One or more sealing rings 233 (e.g., O-rings) can at least partially surround valve stem 221 to restrict the flow of fluid out of flow path 206 in the area of valve stem 221. In addition, a weep hole 235 can be provided to further remove any moisture of other fluids that may move past sealing rings 233.

A spring 237 can be provided to bias valve stem 221 towards the closed configuration (FIG. 3A) and to ensure that sealing member 223 seats itself properly with port 231. An air inlet 239 can be provided adjacent valve stem 221 to move valve stem 221 from the closed configuration (FIG. 3A) to the open configuration (FIG. 3B). Compressed air or other fluids can be directed through air inlet 239, causing valve stem 221 to move downward as shown in FIG. 3B. As valve stem 221 moves downward, sealing member 223 moves out of engagement with port 231, allowing fluid to pass through port 231 and enter flow path 206 as shown by arrow 241.

FIG. 3C illustrates a two-way valve that is moveable between a closed configuration (not shown) and an open configuration (FIG. 3C). As shown in FIG. 3C, a valve stem 221 with a sealing member 223 can move into an open configuration in the same manner as that shown in FIG. 3B. Such a valve can be used, for example, with a port 231 that is configured to be opened and closed to allow fluid to flow into the pathway, such as a sanitizing fluid inlet port or a waste outlet port.

Figure 4:
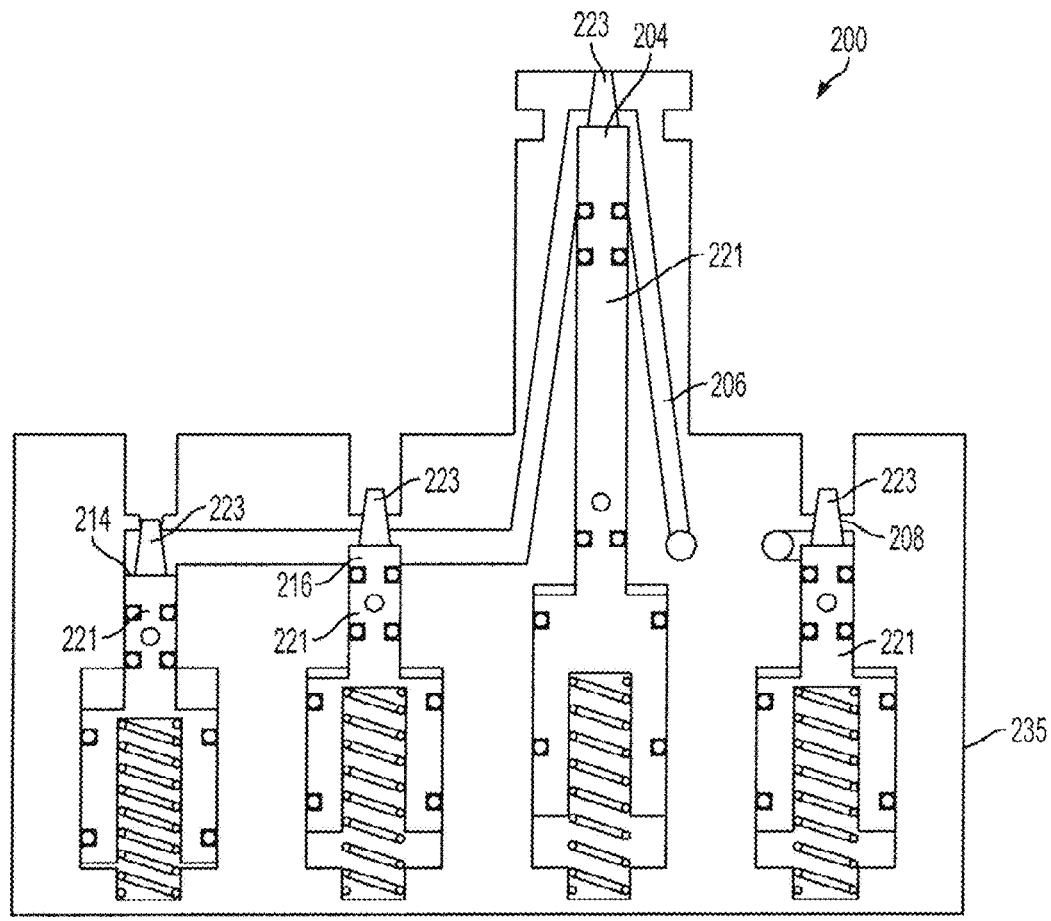
FIG. 4 illustrates a cross-sectional view of a system for obtaining samples from enclosed containers.

FIG. 4 illustrates a cross-sectional view of a portion of another exemplary sampling system 200, shown with an angled fluid path 206 between the sanitizing fluid inlet valve 214 and the outlet valve 208. Sample collection valve 204 extends from a main body 235 of sampling system 200 to facilitate coupling of sample collection valve 204 with bioreactor 202 (not shown in FIG. 4).

Figure 5:
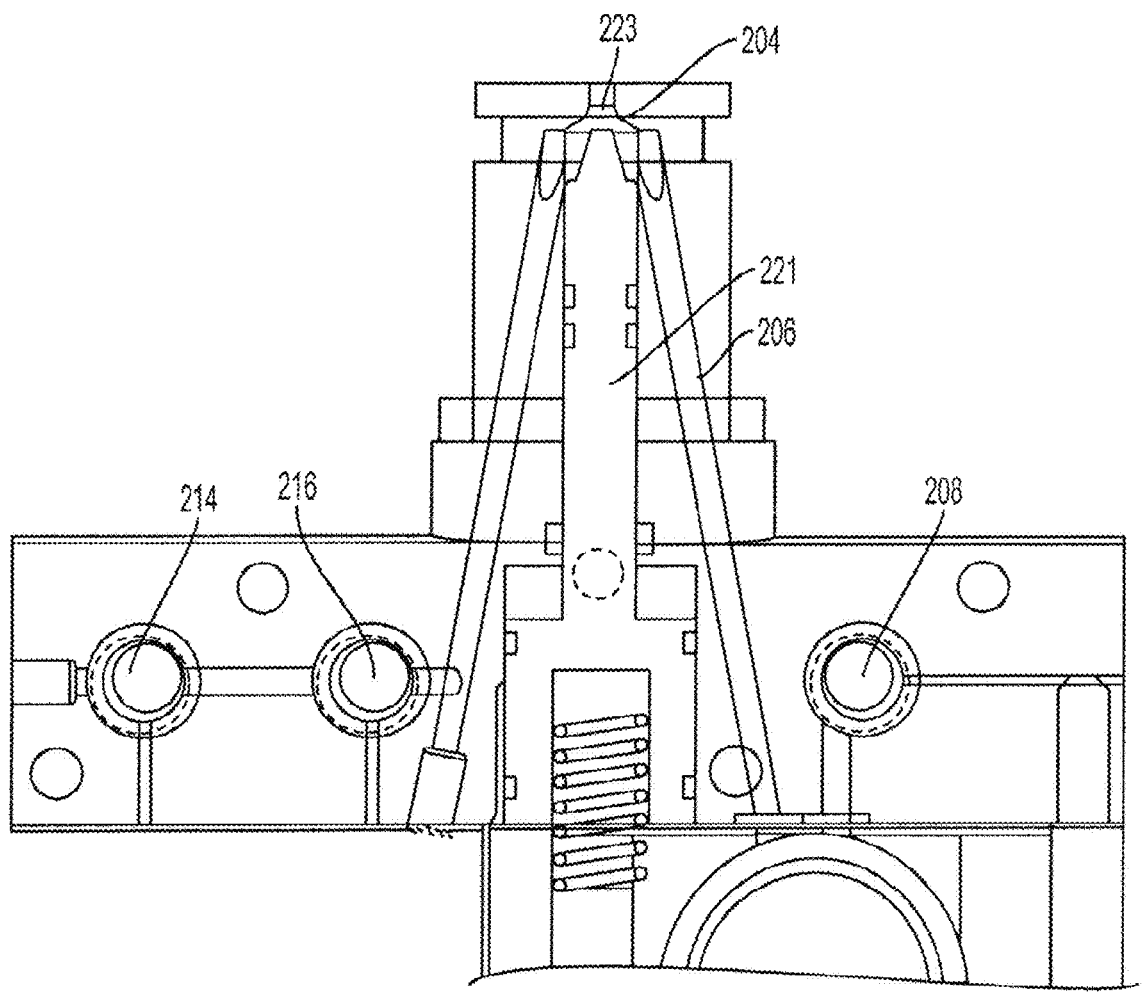
FIG. 5 illustrates a partial cross-sectional view of a system for obtaining samples from enclosed containers.
Figure 6:
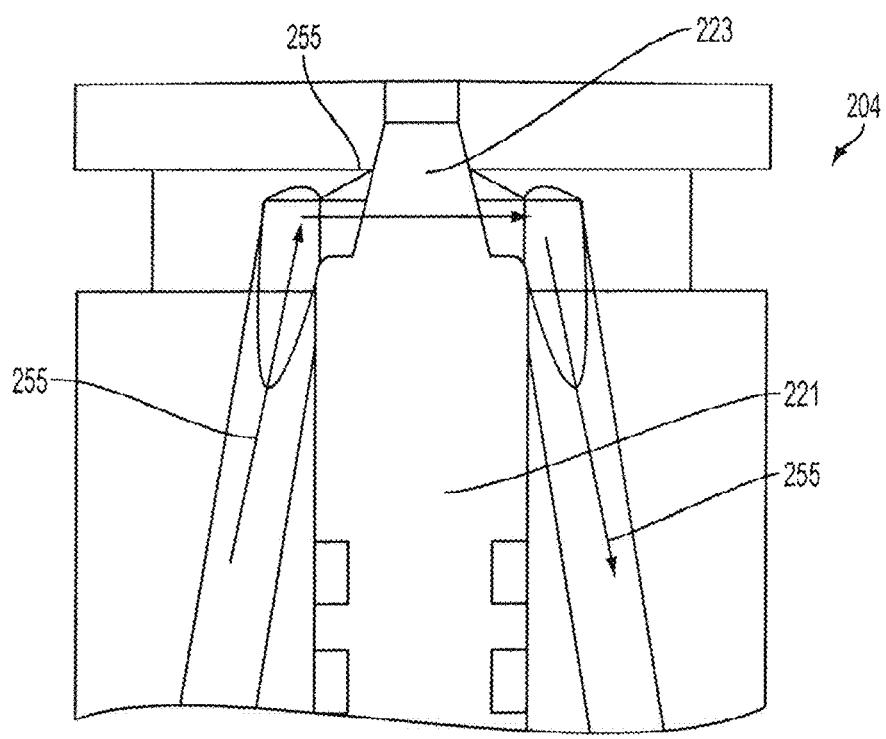
FIG. 6 is an enlarged view of a portion of the system shown in FIG. 4.

FIGS. 5 and 6 illustrate views of portions of another exemplary sampling system 200, also having an angled fluid path 206 between the sanitizing fluid inlet valve 214 and the outlet valve 208. As shown in the enlarged partial cross-sectional view of FIG. 6, when sample collection valve 204 is in a closed position (e.g., with a sealing member 223 extending into an opening between the bioreactor and flow path 206), sanitizing fluid can flow around the end of valve stem 221. Thus, for example, as shown by arrows 255, sanitizing fluid can pass around a portion of sample collection valve 204, thereby improving sanitization or sterilization of the area adjacent the opening extending into the bioreactor.

Moreover, by forming sample collection valve with a sealing member 223 that tapers from valve stem 221, the area of contact between sealing member 223 and the opening can be reduced. To provide improved sealing characteristics, in some embodiments, the tip of the valve stem can extend at an angle of greater than 50 degrees from the body of the valve stem and, more preferably at an angle of greater than 70 degrees and, even more preferably at an angle of about 80 degrees.

In some embodiments, sealing member 223 (FIG. 6) can be formed of a polymeric material that is softer than the material of the seat, into which sealing member 223 extends. In some embodiments, the seat can be formed of a more rigid polymer material. For example, the seat can be made of most teflons (PTFE, PFA, ETFE, etc.) and the seat can be made of a high performance, high temperature, harder thermoplastic. (PEEK, PEI, PPSU, PSU, etc.). For the stem, creep resistant PFA is preferred and PEEK is preferred for the rest of the body. PEEK and teflons are preferable materials due to their relatively chemically inert behavior.

In this manner, sealing member 223 can extrude into the seat to form a tighter seal. In addition, as shown in FIG. 5, sealing member 223 can have a steeper cone shape than the hollow cone seat, thereby allowing sealing member 223 to extrude into the seat to form a positive seal. The design allows for a variable sealing area, causing the stem to deform until the stress on the materials at the seal is within the elastic modulus of the valve stem, allowing a good seal even with relatively wide tolerances on the angles of the seat and stem. This configuration can have several advantages. For example, because the seat can be formed as a cone-shaped hole as shown in FIG. 5, the opening can be very small, allowing it to be easily incorporated into a small conduit and amenable to sterilization in the manners described herein (e.g., by steam). Moreover, when one or both of the sealing member and seat are formed of polymers, the heat up and cool down times associated with those parts can be faster than the times associated with other materials, such as steel or other metals.

In some embodiments, the sealing member and valve stem can be formed of the same polymeric material, which can further improve operation by reducing complexities of manufacturing and permitting the sealing member and valve stem component to be more compact.

Figure 7:
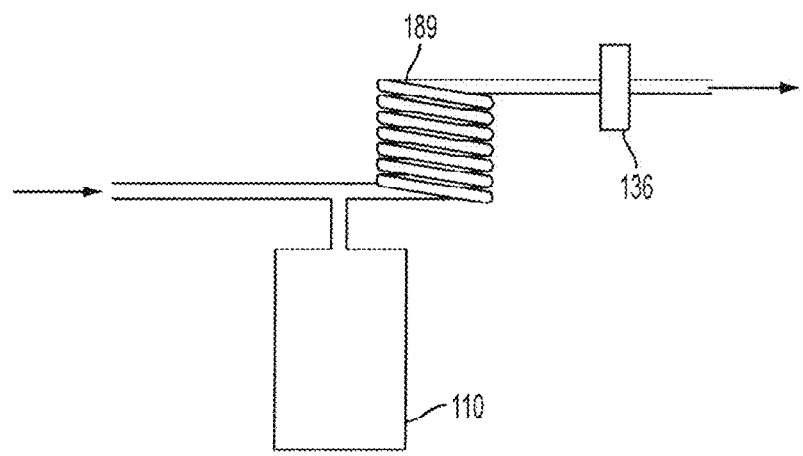
FIG. 7 illustrates a partial view of a portion of a system for obtaining samples from enclosed containers.
Figure 8:
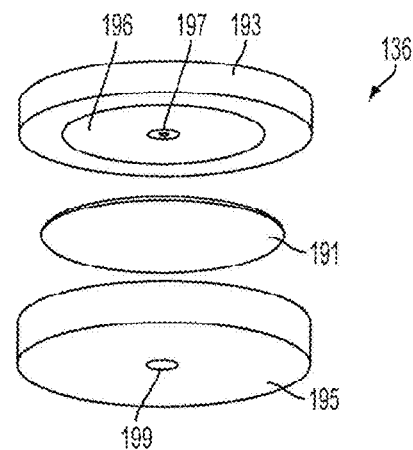
FIG. 8 illustrates a control valve for use with a system for obtaining samples from enclosed containers.
Figure 9:
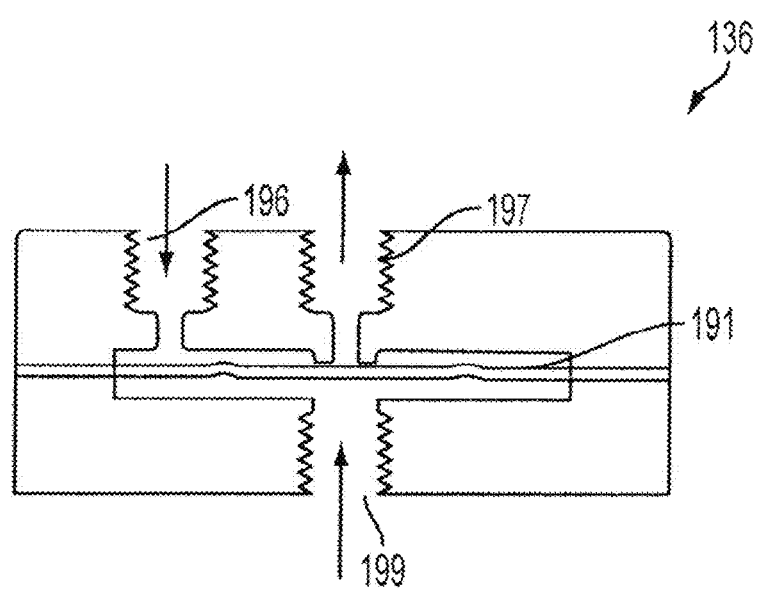
FIG. 9 illustrates another view of the control valve of FIG. 7.
Figure 10:
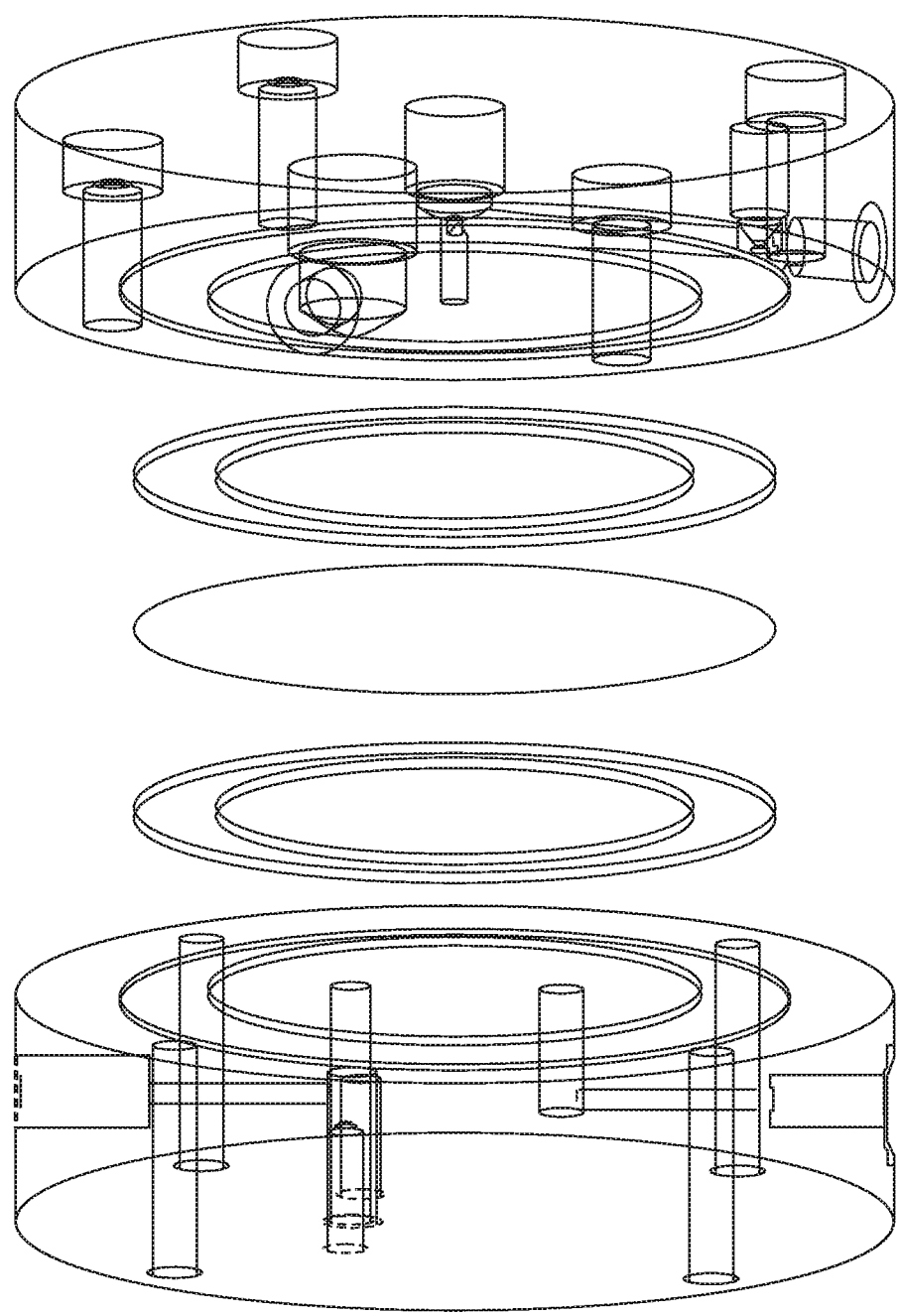
FIG. 10 illustrates another control valve for use with a system for obtaining samples from enclosed containers.
Figure 11:
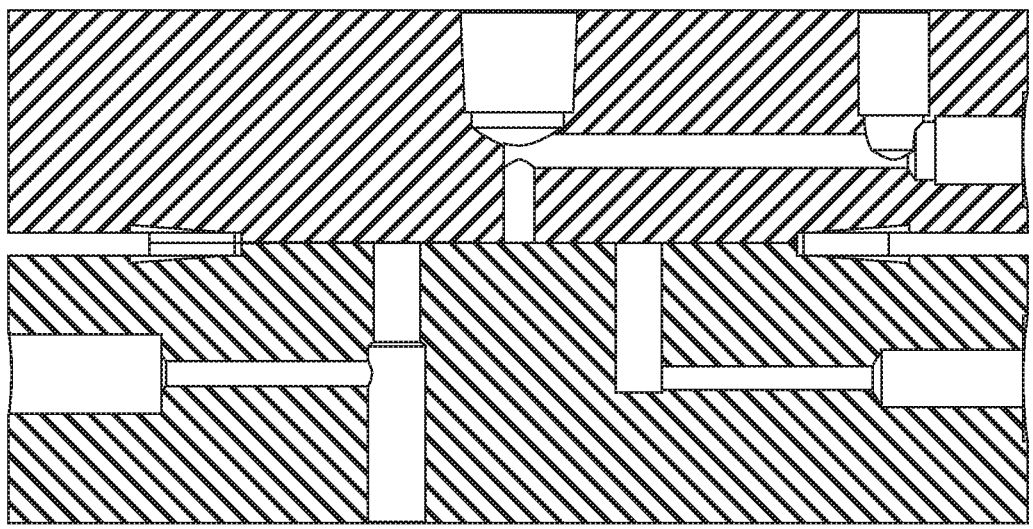
FIG. 11 illustrates a cross-sectional view of the valve shown in FIG. 10.
Figure 12:
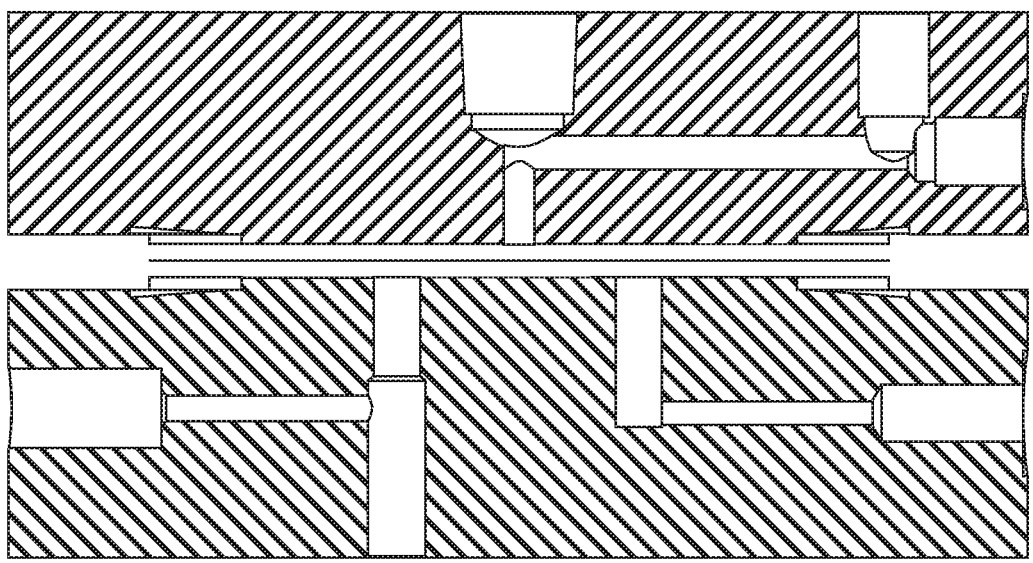
FIG. 12 illustrates a cross-sectional view of the valve shown in FIG. 10.
Figure 13:
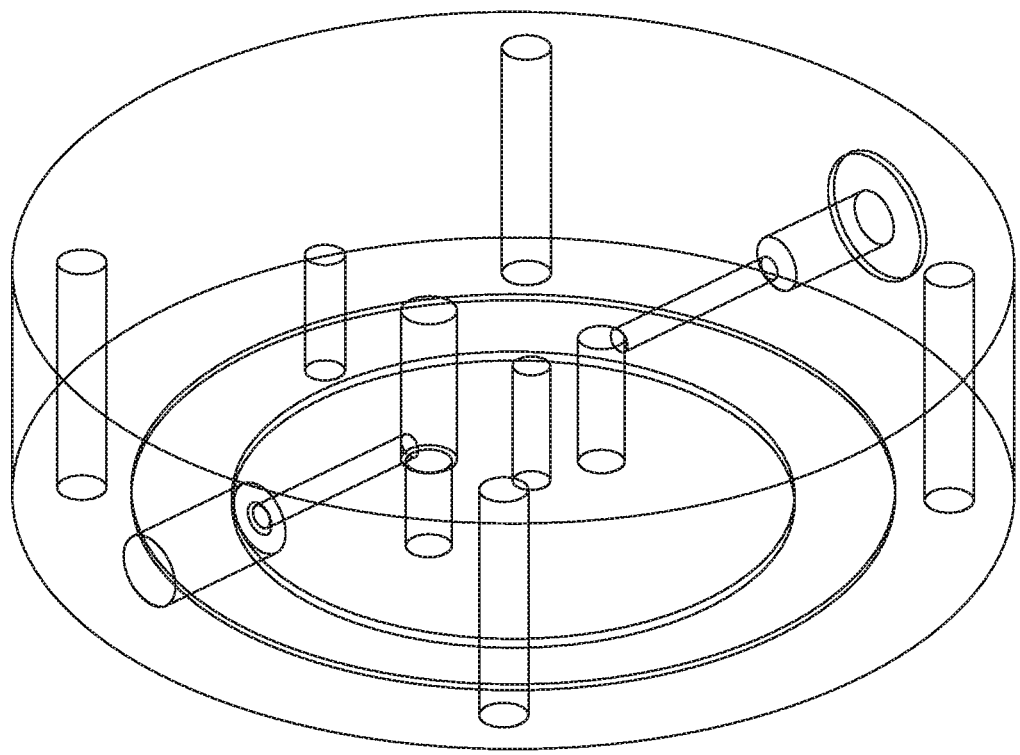
FIG. 13 illustrates the control valve of FIG. 10 shown from a liquid side.
Figure 14:
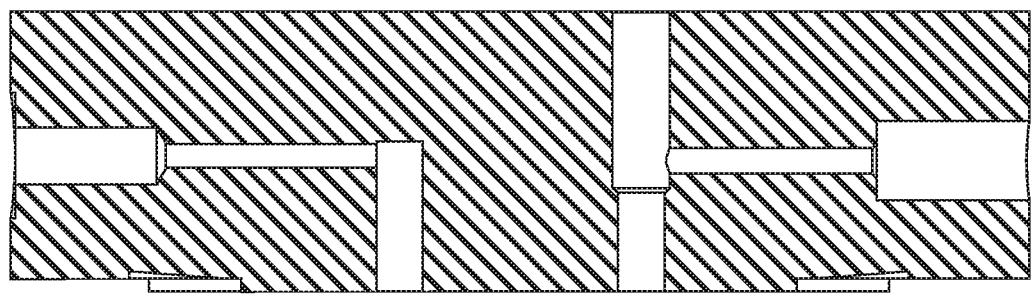
FIG. 14 illustrates a cross-sectional view of the valve of FIG. 10.

FIGS. 7-9 illustrate an embodiment of a valve 136 (or a valve downstream of valve 136) in embodiments when that valve functions as a control valve. As shown in FIGS. 8 and 9, control valve 136 can comprise a diaphragm 191 positioned between two wall members 193, 195 to restrict and/or allow flow through the control valve. For example, first wall member 193 can comprise an inlet 196 and an outlet 197. Movement of diaphragm 191 towards first wall member 193 restricts passage of fluid through inlet 196 and outlet 197. To provide for movement of diaphragm 191, a control air inlet 199 can be provided on the opposing second wall member 195. An increase in air pressure at control air inlet 199 causes diaphragm 191 to move towards first wall member 193, while a decrease in air pressure at control air inlet 199 causes diaphragm 191 to move away from first wall member 193. In this manner, back pressure can be adjusted adjacent the outlet valve of the sampling system as needed or desired.

Referring again to FIG. 7, a holding coil 189 can be provided to contain a sample during a sample collection processing. Holding coil 189 can provide a volume into which a sample can be drawn. In operation, the sample is pumped or drawn into holding coil 189 and then drawn into the chamber from holding coil 189. This can allow larger samples to be drawn and, if the sample drawn is larger than the sample delivered into chamber 110, ensure that the sample delivered into chamber 110 is from a central region of the drawn sample. By capturing a central portion of the sample, the likelihood of that sample being contaminated within the flow path of the sampling system can be further reduced.

Some features of the design of the AAS and its sample cycle are provided below.

Design
  Current Good Manufacturing Practice (cGMP) compliant
  OPC communication capable for integration with variety of analyzers and devices
  Unique valve design
  Scheduler with operator-specified sampling intervals
Sample Cycle (<45 Minutes)
  SIP for Sterilization
  Cool down followed by condensate purge
  Sample draw
  Sample dispense to sample-handling device or directly to analytical instrument The automated sampling systems described herein can advantageously allow for more frequent collection of data, reduce sampling variation and human error associated with the capturing of samples, and reduce costs by reducing labor requirements associated with manual sampling.

Figure 18:
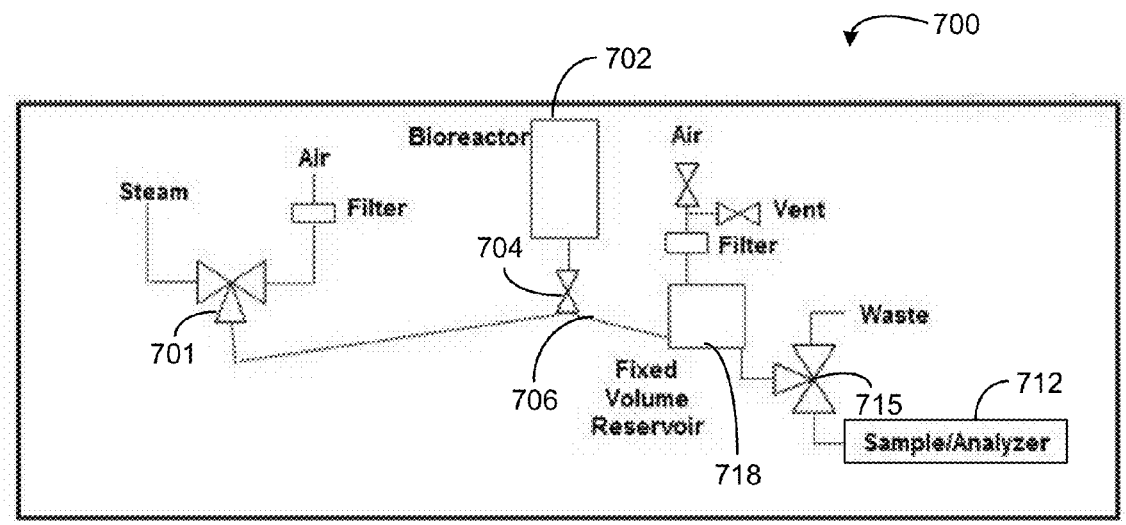
FIG. 18 illustrates a schematic view of an exemplary sampling system for obtaining samples from enclosed containers using fixed volume reservoirs.
Figure 19:
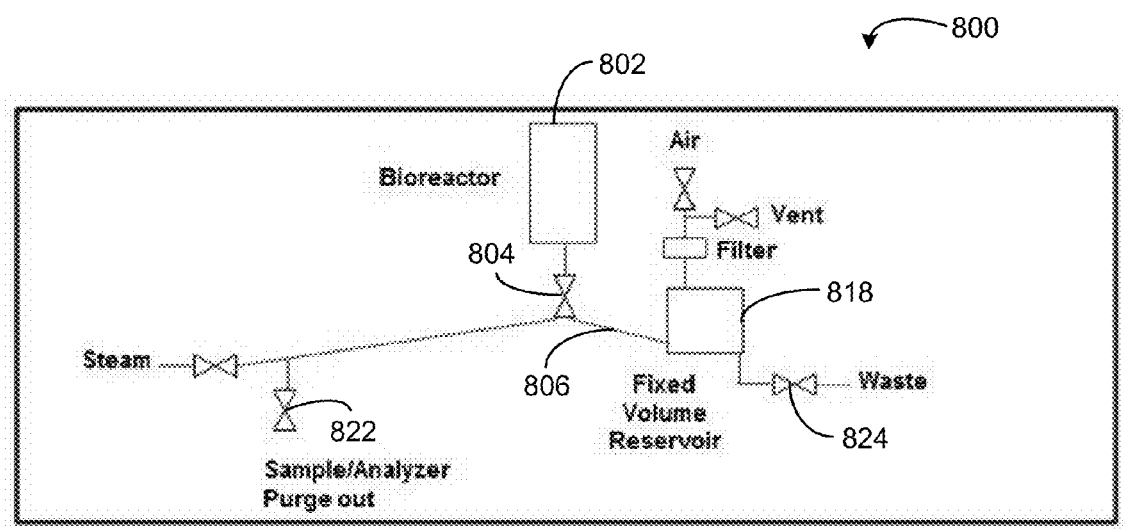
FIG. 19 illustrates a schematic view of an exemplary sampling system for obtaining samples from enclosed containers using fixed volume reservoirs.
Figure 20:
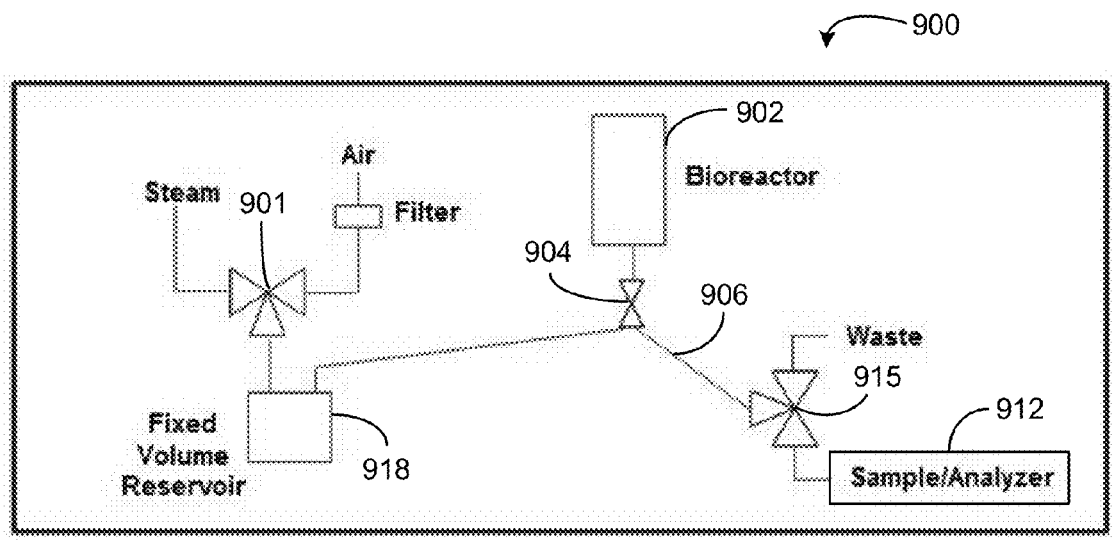
FIG. 20 illustrates a schematic view of an exemplary sampling system for obtaining samples from enclosed containers using fixed volume reservoirs.

It should be understood that the various steps of the disclosed methods and the various components of the disclosed apparatuses are exemplary and the particular order of steps and arrangement of components can be varied without departing from the scope of the invention. For example, FIGS. 18-20 illustrate additional embodiments with various components of the apparatus rearranged, resulting in variations in the order and/or manner in which the steps of the respective methods are performed. These additional embodiments are merely examples of some of the manners in which the steps and/or components of the disclosed embodiments can be rearranged without departing from the scope of the invention. Other rearrangement of steps and/or components are contemplated.

Figure 15:
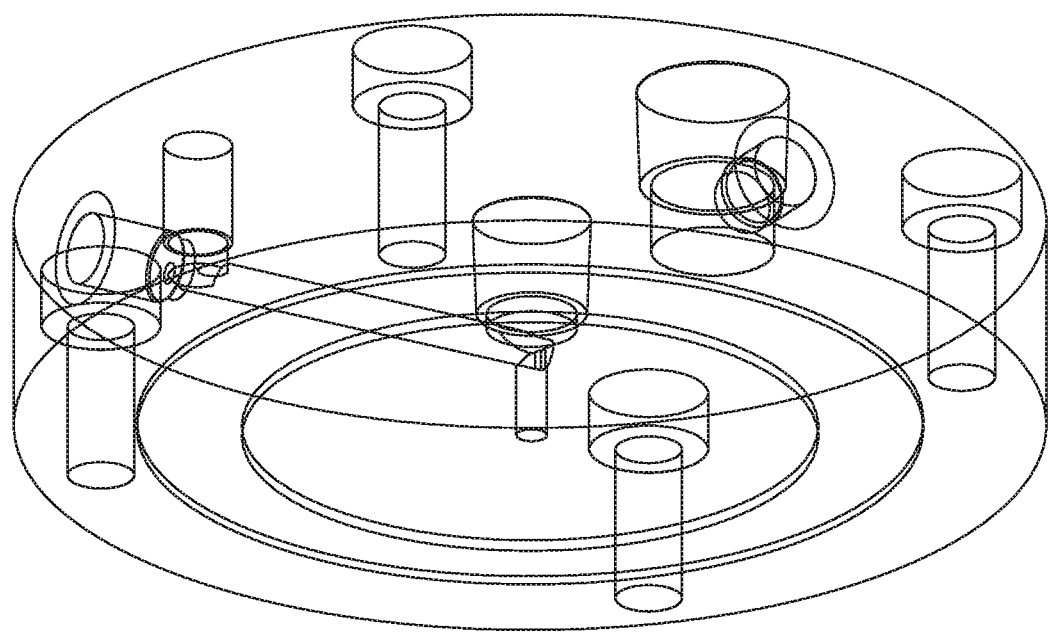
FIG. 15 illustrates the control valve of FIG. 10 shown from an air side.
Figure 16:
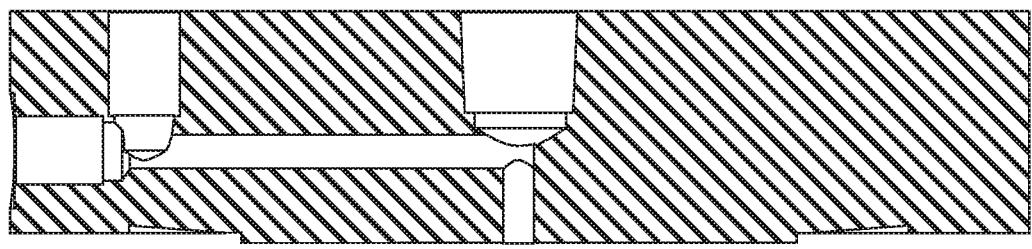
FIG. 16 illustrates a cross-sectional view of the valve of FIG. 10.
Figure 17:
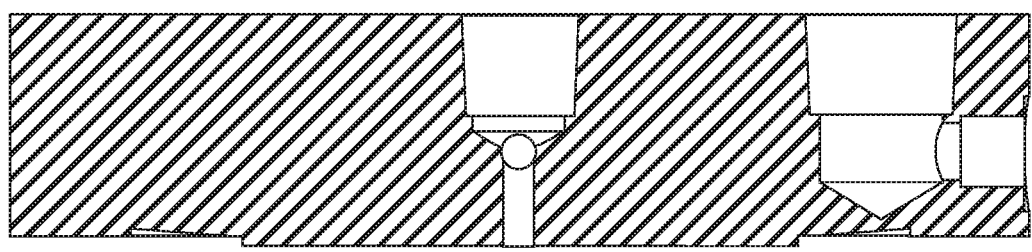
FIG. 17 illustrates a cross-sectional view of the valve of FIG. 10.

FIGS. 10-17 illustrate an exemplary control valve for use with the systems disclosed herein for obtaining samples from enclosed containers. As described elsewhere herein, the control valve illustrated in FIGS. 11-18 can be provided downstream of the outlet valve to provide a back pressure to the sample and/or sanitizing fluid. Sample and/or sanitizing fluid/purge gas engages with the "liquid side" of the control valve (FIGS. 13 and 14) and control air engages with the "air side" of the control valve (FIGS. 15-17). A diaphragm positioned between the two sides (shown in FIG. 10) moves between the two sides to either allow flow through the liquid side of the control valve or to restrict that flow. Thus, when control air engages with the "air side," the valve is closed and no sample, sanitizing fluid, or purge gas can pass through the valve. When control air does not engage with the "air side" (or at least not with enough pressure to maintain the diaphragm in the closed position), the control valve is open and sample, sanitizing fluid, or purge gas can pass through the valve.

Thus, the control valve illustrated in FIGS. 10-17 functions as a pressure regulator by cutting off the flow of liquid or gas when a certain control air pressure is achieved.

Exemplary Fixed Volume Sampling Devices

Referring to FIG. 18, apparatus 700 comprises a bioreactor 702 coupled to a sample collection valve 704. The sanitizing fluid (e.g., steam) and purge fluid (e.g., air) can be delivered into fluid flow path 706 at a common location (e.g., via a three-way valve 701). Because contents of bioreactors are usually under pressure, when sample collection valve 704 is opened a sample of those contents will be directed along fluid flow path 706 into fixed volume reservoir 718. As discussed below, alternatively or additionally, one or more pump devices can be provided to either push or pull the sample along the fluid flow path.

As the fixed volume reservoir 718 is filled, gas from within the reservoir can be pushed out and vented through the vent shown in FIG. 18. If desired gas can be filtered as it is vented. Once the sample is drawn into reservoir 718, sample collection valve 704 can be closed. After closing sample collection valve 704, the sample can be discharged to an analyzer and/or for disposal as desired.

For example, a three-way valve 715 can be provided downstream from reservoir 718, with valve 715 being configured to permit delivery of a sample and/or other materials in fluid flow path 706 through valve 715 to an analyzer 712 or, alternatively, to a waste collection area. The sample can be discharged from reservoir 718 in various manners. For example, it can be forced out through the introduction of gas into the reservoir (e.g., via an air delivery means as shown in FIG. 18).

After sample collection, valve 715 can move to a second configuration which restricts fluid flow to analyzer 712 and permits fluids in the flow path 706 (e.g., sanitizing fluid and purging gas) to be directed to a waste collection area. Thus, for example, as described elsewhere herein, fluid flow path 706 can be sanitized using steam and air (or other sanitizing fluids and purging gases) that is delivered from upstream of fluid flow path 706.

FIG. 19 illustrates another exemplary sampling apparatus 800 for use with a fixed volume reservoir 818. As in the previous system described herein, apparatus 800 comprises a bioreactor 802 coupled to a sample collection valve 804. In this embodiment, the sanitizing fluid inlet (e.g., steam) is positioned upstream of sample collection valve 804 and the purging fluid inlet (e.g., air) is positioned downstream of sample collection valve 804.

In operation, reservoir 818 can draw a sample "downstream" through sample collection valve 804. A described above, by opening the sample collection valve, contents under pressure in bioreactor 802 can be discharged to reservoir 818. Once the sample is drawn, sample collection valve 804 can close. Reservoir 818 can then deliver the sample "upstream" along fluid flow path 806 towards valve 822. The delivery of sample upstream can be achieved, for example, by pumping the sample upstream from reservoir 818.

Valve 822 can be opened to permit delivery of the sample through valve 822 to an analyzer. Thus, when capturing a sample, the system delivers the sample "downstream" into reservoir 818 and then the sample is delivered at least partially back "upstream" through valve 822 to the analyzer. After sample collection and delivery to the analyzer, valve 822 is closed so that sanitizing fluid (e.g., steam) can then be introduced, through a valve, into fluid flow path 806 to sanitize fluid flow path 806.

After sanitization, a purge fluid (e.g., air) can be delivered into the fluid flow path 806 and valve 824 can be opened to allow waste discharge and, concurrently or subsequently, valve 822 can be opened to allow the gas to be purged out fluid flow path 806.

FIG. 20 illustrates another exemplary sampling apparatus 900. Apparatus 900 comprises a bioreactor 902 coupled to a sample collection valve 904. Unlike other embodiments disclosed herein, fixed volume reservoir 918 can draw a sample "upstream" through sample collection valve 904. To draw the sample upstream, a pump can be provided that pushes or pulls the sample in the desired direction. For example, a pump (e.g., a diaphragm pump, peristaltic pump, gear pump) can be positioned along the fluid flow path to cause the sample to be delivered (e.g., pushed or pulled) in the desired direction.

Once the sample is drawn, the sample collection valve 904 can close and reservoir 918 can discharge the sample back "downstream" along fluid flow path 906 towards a three-way valve 915 that is provided downstream from reservoir 918. Valve 915, can be configured to permit delivery of the sample and/or other materials in the fluid flow path 906 through valve 915 to an analyzer 912 or to discharge as waste.

Thus, in operation, when capturing a sample, the system draws the sample "upstream" into reservoir 918 and reservoir 918 then delivers the sample through valve 915 to analyzer 912. After sample collection and discharge to analyzer 912, valve 915 can restrict fluid flow to analyzer 912 and instead direct fluids in the flow path 906 (e.g., sanitizing fluid and purging gas) through valve 915 to a different path for waste collection.

In some embodiments, the delivery of the sample along the fluid flow path can be achieved using the positive pressure of contents in the bioreactor. Thus, for example, opening the sample collection valve can cause a sample in the bioreactor to be discharged downstream towards a reservoir. Alternatively or additionally, as discussed above, for each of the fixed volume reservoir embodiments, a pump (e.g., a diaphragm pump, peristaltic pump, gear pump) or other such device can be provided to push or pull a sample into the reservoir and/or to discharge the sample from the reservoir. The pump can be positioned along the fluid flow path so that it can cause a positive or negative pressure sufficient to push or pull the sample as desired. For example, with reference to FIG. 18, a pump can be positioned downstream of sample collection valve 704 (e.g., between sample collection valve 704 and reservoir 718, or downstream of reservoir 716 such as along the waste path) or upstream of sample collection valve 704 (e.g., between sample collection valve 704 and valve 701) to cause the sample to be received in the reservoir and delivered to an analyzer as described herein.

Figure 21:
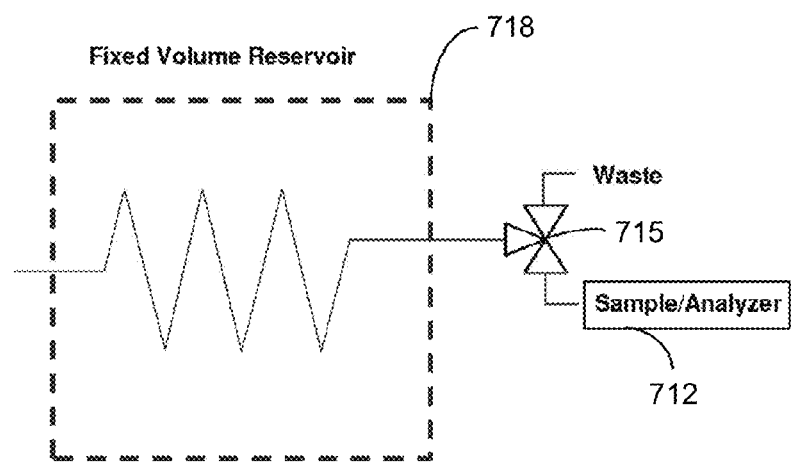
FIG. 21 illustrates a schematic view of an exemplary fixed volume reservoir.

The fixed volume reservoirs described herein can comprise any structure capable of holding a predetermined amount of sample. For example, as shown in FIG. 21, the fixed volume reservoir can be defined by a length of tubing that can hold a predetermined amount of sample. The tubing can be formed in any length and shape, including the zigzag shape shown in FIG. 21. Other shapes of tubing that define the fixed volume reservoir include, for example, straight tubes, loops, coiled shapes, and/or any combination of these shapes.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A sampling system for collecting a fluid sample from an enclosed container, the system comprising:
   (a) a sanitizing fluid inlet valve;
   (b) a gas inlet valve;
   (c) a sample collection valve having a valve stem, the sample collection valve being operable between an open position and a closed position;
   (d) a first outlet valve operable between an open position and a closed position;
   (e) a fixed volume reservoir; and
   (f) a second outlet valve operable between an open position and a closed position;
   (g) a fluid flow path interconnecting (a)-(f),
   wherein when (a) and (b) are oriented to restrict flow of the sanitizing fluid and gas through the respective valves, (f) is in the closed position, and (d) is in the open position, (c) can be in the open position to withdraw a sample from the enclosed container into the reservoir along a first portion of the fluid flow path,
   wherein when (a) and (c) are oriented to restrict flow of the sanitizing fluid and sample through the respective valves, (f) is in the closed position, and (b) is in the open position, the sample can be discharged from the reservoir along a second portion of the fluid flow path through (d), and
   wherein when (a) is oriented to permit flow of the sanitizing fluid through the sanitizing fluid inlet valve, (b) is oriented to restrict flow of the gas through the gas inlet valve, and (c) is in the closed position, a sanitizing fluid can be introduced into the fluid flow path through (a) to sanitize at least the first portion of the fluid flow path and a portion of the valve stem that extends into a fluid flow path when (c) is in the closed position,
   wherein (b) is at an upstream portion of the fluid flow path relative to (c), and when (b) is in an open position and (c) is in a closed position, a gas can flow through (b) into the first portion of the fluid flow path and past the valve stem.

2. The sampling system of claim 1, wherein when (a) is in the open position and (b) and (c) are in the closed position, the sanitizing fluid also sanitizes the reservoir.

3. The sampling system of claim 1, wherein (a) is at an upstream portion of the fluid flow path and (d) is at a downstream portion of the fluid flow path, and the sanitizing fluid can flow through the fluid flow path from (a) to (f) to sanitize the fluid flow path between (a) and (f).

4. The sampling system of claim 3, wherein (a)-(f) are interconnected along the fluid flow path from the upstream portion to the downstream portion in the following order: (a), (b), (c), (e), (d), and (f).

5. The sampling system of claim 1, wherein the sanitizing fluid inlet valve is operable between an open position and a closed position, the gas inlet valve is operable between an open position and a closed position, and the sanitizing fluid inlet valve and gas inlet valve are separate valves.

6. The sampling system of claim 1, wherein the sanitizing fluid inlet valve and the gas inlet valve are coupled via a three-way valve, the three way valve being operable between a first position that permits the flow of sanitizing fluid through the sanitizing fluid inlet into the fluid flow path, a second position that permits the flow of gas through the gas inlet into the fluid flow path, and a third position that restricts the flow of both sanitizing fluid and gas into the fluid flow path.

7. The sampling system of claim 1, the second outlet valve (f) being located downstream of the first outlet valve (d), wherein when (a) is oriented to permit flow of the sanitizing fluid through the sanitizing fluid inlet valve, (b) is oriented to restrict flow of the gas through the gas inlet valve, and (c) and (d) are in the closed position, the sanitizing fluid can flow along the fluid flow path between (a) and the second outlet valve (f) to sanitize portions of the fluid flow path in the vicinity of (c) and (d).

8. The sampling system of claim 7, wherein the second outlet valve (f) comprises a variable back-pressure regulator.

9. The sampling system of claim 7, wherein when (a) is oriented to restrict flow of the sanitizing fluid through the sanitizing fluid inlet valve and (c) is in the closed position, (b) is oriented to permit flow of the gas through the gas inlet valve, (d) is in the closed position, and (f) is in the open position, gas can be introduced into the fluid flow path through (b) to purge the sanitizing fluid from at least the first and second portions of the fluid flow path.

10. The sampling system of claim 1, wherein the valve stem has a tapered sealing member.

11. A method of collecting a fluid sample from an enclosed container, the method comprising:
opening a sanitizing fluid inlet valve and directing sanitizing fluid downstream through a fluid flow path past a closed sample collection valve and a closed first outlet valve, the sanitizing fluid contacting the closed sample collection valve to sanitize the sample collection valve;
discharging the sanitizing fluid out a second outlet valve, the second outlet valve being located downstream of the first outlet valve;
opening a sample collection valve while the sanitizing fluid inlet valve and first outlet valve are closed;
drawing a fluid sample from the enclosed container into a fixed volume reservoir along a first portion of the fluid flow path;
directing the fluid sample out of the reservoir along a second portion of the fluid flow path;
discharging the fluid sample out of the first outlet valve while the sanitizing fluid inlet valve and sample collection valve are closed, and
after discharging the sanitizing fluid but before drawing the fluid sample, opening a gas inlet valve and directing a gas downstream through the fluid flow path past the closed sample collection valve and through the first open outlet valve, and discharging the gas through the second outlet valve to purge the sanitizing fluid from at least the first and second portions of the fluid flow path.

12. The method of claim 11, wherein the reservoir comprises a pump that is configured to draw the sample into the reservoir through a reservoir inlet and direct the sample out of the reservoir through a reservoir outlet.

13. The method of claim 11, wherein the sanitizing fluid comprises steam.

14. A sampling system for collecting a fluid sample from an enclosed container, the system comprising:
(a) a sample collection valve operable between an open position and a closed position;
(b) a first outlet valve operable between a waste delivery position and a non-waste delivery position;
(c) a fixed volume reservoir;
(d) a fluid flow path interconnecting the sample collection valve, first outlet valve, and the fixed volume reservoir;
(e) a sanitizing fluid inlet into the fluid flow path; and
(f) a gas inlet into the fluid flow path;
wherein the fixed volume reservoir can withdraw a sample from the enclosed container along the fluid flow path and into the fixed volume reservoir when the sample collection valve is in the open position and the first outlet valve is in the non-waste delivery position, and the fixed volume reservoir can discharge the sample from the fixed volume reservoir and out of the fluid flow path of the sampling system for subsequent analysis when the sample collection valve is in the closed position,
wherein, after discharge of the sample for subsequent analysis and with the first outlet valve in the non-waste delivery position, a sanitizing fluid can be introduced into the fluid flow path via the sanitizing fluid inlet to sanitize the sample collection valve when it is in the closed position, and
wherein, after sanitizing the apparatus, the first outlet valve can be moved to the waste delivery position and a gas can be introduced into the fluid flow path, directed across at least a portion of the sample collection valve when it is in the closed position, and discharged out the first outlet valve.

15. The sampling system of claim 14, wherein the sanitizing fluid inlet is at an upstream portion of the fluid flow path and the first outlet valve is at a downstream portion of the fluid flow path, and the sanitizing fluid can flow through the fluid flow path from between the sanitizing fluid inlet to the first outlet valve to sanitize the fluid flow path therebetween.

16. The sampling system of claim 14, wherein the sanitizing fluid inlet and the gas inlet are coupled via a three-way valve, the three way valve being operable between a first position that permits the flow of sanitizing fluid through the sanitizing fluid inlet into the fluid flow path, a second position that permits the flow of gas through the gas inlet into the fluid flow path, and a third position that restricts the flow of both sanitizing fluid and gas into the fluid flow path.

17. The sampling system of claim 14, wherein the non-waste delivery position of the first outlet valve comprises a first orientation wherein the sample in the fluid flow path can pass through the first outlet valve for subsequent analysis and a second orientation wherein no fluid can pass through the first outlet valve.

18. The sampling system of claim 14, wherein the fixed volume reservoir is downstream of the sample collection valve.

19. The sampling system of claim 14, wherein the fixed volume reservoir is upstream of the sample collection valve.

20. The sampling system of claim 14, wherein the sanitizing fluid inlet and gas inlet are both positioned upstream of the sample collection valve.

* * * * *